United States Patent
Batista

(10) Patent No.: US 10,888,121 B2
(45) Date of Patent: Jan. 12, 2021

(54) E-LIQUID COLLAPSIBLE CARTRIDGE

(71) Applicant: Philip Morris Products S.A., Neuchatel (CH)

(72) Inventor: Rui Nuno Batista, Morges (CH)

(73) Assignee: Philip Morris Products S.A., Neuchatel (CH)

(*) Notice: Subject to any disclaimer, the term of this patent is extended or adjusted under 35 U.S.C. 154(b) by 486 days.

(21) Appl. No.: 15/533,410

(22) PCT Filed: Dec. 14, 2015

(86) PCT No.: PCT/EP2015/079650
§ 371 (c)(1),
(2) Date: Jun. 6, 2017

(87) PCT Pub. No.: WO2016/096762
PCT Pub. Date: Jun. 23, 2016

(65) Prior Publication Data
US 2018/0035717 A1    Feb. 8, 2018

(30) Foreign Application Priority Data
Dec. 15, 2014   (EP) .................................... 14198015

(51) Int. Cl.
*A24F 47/00* (2020.01)
*A24F 40/44* (2020.01)
(Continued)

(52) U.S. Cl.
CPC ............ *A24F 47/008* (2013.01); *A24F 40/44* (2020.01); *B65D 35/38* (2013.01); *H05B 3/46* (2013.01); *H05B 2203/021* (2013.01)

(58) Field of Classification Search
None
See application file for complete search history.

(56) References Cited

U.S. PATENT DOCUMENTS 3,838,796 A * 10/1974 Cohen ................ B65D 83/0077
                                                         222/105
5,518,179 A * 5/1996 Humberstone ..... B05B 17/0646
                                                         239/102.2
(Continued)

FOREIGN PATENT DOCUMENTS

CN    1291957 A    4/2001
CN    1705595 A    12/2005
(Continued)

OTHER PUBLICATIONS

International Search Report and Written Opinion dated Mar. 31, 2016 in PCT/EP2015/079650, filed Dec. 14, 2015.
(Continued)

*Primary Examiner* — Thor S Campbell
(74) *Attorney, Agent, or Firm* — Oblon, McClelland, Maier & Neustadt, L.L.P.

(57) ABSTRACT

A cartridge for an aerosol generating system is provided, including a liquid storage portion including a rigid support portion having a nozzle defining an opening configured to dispense an aerosol-forming substrate and a collapsible portion, attached to the rigid support portion; and a wick disposed in the nozzle, extending across a full cross-section of the opening. An aerosol generating system is also provided, including the cartridge; and a method is provided for forming the cartridge including providing a rigid support portion with a nozzle defining an opening; attaching a collapsible portion to the rigid support portion to form a liquid storage portion; and providing a wick in the nozzle, the wick extending across a full cross-section of the opening.

15 Claims, 4 Drawing Sheets

(51) Int. Cl.
*H05B 3/46* (2006.01)
*B65D 35/38* (2006.01)

(56) References Cited

U.S. PATENT DOCUMENTS

| | | | |
|---|---|---|---|
| 5,894,841 A | 4/1999 | Voges | |
| 6,443,146 B1* | 9/2002 | Voges | A24F 47/002 |
| | | | 128/200.14 |
| 6,460,781 B1 | 10/2002 | Garcia et al. | |
| 9,757,750 B2* | 9/2017 | Holakovsky | A61M 15/0065 |
| 10,016,568 B2* | 7/2018 | Bach | A61M 15/0065 |
| 2003/0015605 A1 | 1/2003 | Garcia et al. | |
| 2003/0075188 A1* | 4/2003 | Adiga | A24F 47/004 |
| | | | 131/185 |
| 2004/0143235 A1* | 7/2004 | Freund | B65D 83/0061 |
| | | | 604/408 |
| 2004/0144811 A1 | 7/2004 | Pennaneac'h | |
| 2005/0175331 A1* | 8/2005 | Tam | A01M 1/2072 |
| | | | 392/405 |
| 2005/0258272 A1* | 11/2005 | Salvage | B05B 11/00412 |
| | | | 239/328 |
| 2006/0180143 A1* | 8/2006 | Lind | A61M 15/02 |
| | | | 128/200.14 |
| 2006/0196518 A1 | 9/2006 | Hon | |
| 2008/0315011 A1* | 12/2008 | Pesu | A01M 1/205 |
| | | | 239/136 |
| 2011/0168175 A1* | 7/2011 | Dunne | A61M 11/02 |
| | | | 128/203.12 |
| 2012/0090603 A1* | 4/2012 | Dunne | A61M 11/06 |
| | | | 128/200.22 |
| 2012/0090630 A1 | 4/2012 | Hon | |
| 2012/0273589 A1 | 11/2012 | Hon | |
| 2012/0318882 A1 | 12/2012 | Abehasera | |
| 2013/0213418 A1 | 8/2013 | Tucker et al. | |
| 2013/0276804 A1 | 10/2013 | Hon | |
| 2014/0034070 A1 | 2/2014 | Schennum | |
| 2014/0069424 A1 | 3/2014 | Poston et al. | |
| 2014/0190496 A1* | 7/2014 | Wensley | A24F 47/008 |
| | | | 131/273 |
| 2014/0261499 A1 | 9/2014 | Hon | |
| 2014/0318560 A1 | 10/2014 | Hon | |
| 2015/0367013 A1* | 12/2015 | Gruenbacher | A45D 34/00 |
| | | | 239/13 |
| 2017/0071249 A1* | 3/2017 | Ampolini | A24F 47/008 |
| 2017/0071255 A1* | 3/2017 | Revell | A24F 47/008 |
| 2017/0172212 A1* | 6/2017 | Phillips | A24F 47/008 |
| 2018/0310616 A1* | 11/2018 | Clemens | A24F 47/008 |

FOREIGN PATENT DOCUMENTS

| | | |
|---|---|---|
| CN | 101986779 A | 3/2011 |
| CN | 103180053 A | 6/2013 |
| EP | 1 618 803 B1 | 12/2008 |
| FR | 2 778 639 A1 | 11/1999 |
| JP | 8-511966 A | 12/1996 |
| WO | WO 2013/083635 A1 | 6/2013 |
| WO | WO 2014/139609 A2 | 9/2014 |

OTHER PUBLICATIONS

Combined Chinese Office Action and Search Report dated Aug. 16, 2019, in Patent Application No. 201580062850.7, 15 pages (with English translation).

English translation of the Japanese Office Action dated Feb. 25, 2020 in Patent Application No. 2017-530660, 12 pages.

* cited by examiner

E-LIQUID COLLAPSIBLE CARTRIDGE

The present invention relates to a cartridge for an aerosol generating system, the cartridge comprising a liquid storage portion with a rigid support portion and a nozzle defining an opening. A wick is provided in the nozzle and facilitates dispensing of the liquid aerosol-generating substrate. The present invention also relates to an aerosol-generating device comprising such cartridge and a method for its manufacture.

Hitherto produced e-cigarettes include an e-liquid tank in which the aerosol-generating liquid is drawn out of the tank by the capillarity action of a wick. The liquid is provided to a heating element which generates an aerosol by application of heat. The aerosol is then inhaled by the e-cigarette user. In order to allow for save handling of the e-liquid, conventionally used reservoirs comprise a rigid container having a fixed shape and volume.

A drawback of such rigid containers is that the decrease of e-liquid in the tank has to be balanced by air coming into the tank. Otherwise, the pressure difference between the outside and inside of the container will prevent the e-liquid to be drawn out by the wick.

The air flow into the tank via the wick evaporates the e-liquid and impairs the capillary activity of the wick. In particular, wettability of the wick and of the heating element is decreased, negatively affecting the flavour of the e-cigarette, the aerosol density and the overall smoking experience.

US 2014 0190496 A1 is directed to an aerosol-generating system comprising a reservoir that is in fluid connection with a heater element via a capillary tube. Upon first use of the system the capillary tube pierces reservoir such that the liquid can enter into the capillary tube. The reservoir may be a collapsible bag or container made from plastic, foil, or any other collapsible material known in the art.

EP 1 618 803 B1 discloses an aerosol-generating device comprising an electro-thermal vaporization nozzle, an electronic valve connected with a metering cavity, and a collapsible liquid storage container. A gas vessel filled with high-pressure nitrogen is arranged around the periphery of the liquid storage container to exert pressure thereon and to facilitate transmission of the liquid. When a control signal is applied to the electronic valve, the electronic valve is activated, and the solution with nicotine enters the metering cavity from the liquid storage container under pressure and pushes a piston so as to allow a constant volume of liquid at the other side of the piston to enter the vaporization nozzle via the electronic valve and be vaporized and condensed to form aerosols. The metering cavity provided at the valve is a cylinder having a liquid inlet and a liquid outlet. The cylinder contains a piston with micro holes and a reset spring connected onto the piston. Due to slow infiltration of the micro holes of the piston in the metering cavity and the force of the reset spring, the piston returns to its original position within 5-8 seconds after each atomization process.

The known aerosol-generating devices with collapsible liquid reservoirs have several drawbacks. They are prone to leakage. The reservoirs are not replaceable. Once pierced by the capillary tube, the reservoir has to be used until the liquid is consumed. It has been found that the quality of aerosol-generating devices crucially depends on the quality of the wick and of the heater elements used. In order to ensure continued high quality aerosol generation, the wick and the heater have to be regularly maintained and replaced, respectively.

One or more of the above mentioned problem may be alleviated by providing a cartridge for an aerosol generating system, comprising a liquid storage portion with a rigid support portion and a collapsible portion, attached to the rigid support portion. The rigid support portion comprises a nozzle defining an opening for dispensing a liquid aerosol-forming substrate. A wick is provided in the nozzle of the rigid support portion.

In the cartridge according to the present invention, the aerosol-generating liquid is drawn out of the liquid storage portion by capillary action of the wick. Due to the fact that the cartridge comprises a collapsible portion, the internal volume of the liquid storage portion will decrease when aerosol-generating liquid is being drawn out. In the cartridge according to the present invention less pressure differences are created between the inside and the outside of the cartridge such that air flow into the cartridge hampering the capillary action of the wick may be avoided and wettability of the wick and the heating element may be increased.

The wick is made from any suitable porous material, preferably made from fibrous material resistant to temperatures up to 300 degree Celsius. The wick is preferably made of such fibers as aramid fibers, glass fibers, carbon fibers, Kevlar fibers, metallic fibers, or a combination of those.

The wick extends across the full cross-section of the opening defined by the nozzle of the rigid support portion of the cartridge. The wick may be tightly held by the nozzle. Additionally the wick may efficiently prevent liquid from dripping out of the cartridge.

The rigid support portion of the cartridge is made from any suitable rigid material. Preferably the material of the rigid support portion is selected from the group of solid polymer material, duroplastic material, thermosetting material, heat resistive material, and ceramic material. Preferably the material of the rigid support portion is a polymer chemically resistant to nicotine, such as acrylonitrile/aethylacrylate copolymer (e.g. commercially available under the brand name barex) or fluorinated ethylene propylene (FEP). Preferably Young's modulus of the rigid material is above 0.5 GPa and preferably ranges between 1 GPa and 5 GPa or between 1.2 GPa and 3 GPa Preferably the rigid support portion comprises an attachment portion for attaching the cartridge in an aerosol forming chamber of an aerosol generating system. The attachment portion can be provided at the nozzle, at the sides or at any other suitable location of the rigid support portion. With the attachment portion the cartridge can releasably be mounted within an aerosol-generating device, such that a cartridge can easily be exchanged when the aerosol-generating liquid is consumed.

Preferably the cartridge comprises a re-closable cap for closing the opening of the nozzle. This embodiment offers the advantage that cartridges can also be exchanged although their content is not yet fully consumed. When a not fully emptied cartridge is removed from the aerosol-generating device, the cartridge is closed with the re-closeable cap to prevent drying out of the remaining liquid content of the cartridge. In this way the user can readily choose from a variety of different e-liquid products and can interchange cartridges at will. Opened cartridges can be re-used at a later stage and it is not required to fully consume a given product before an alternative product can be enjoyed.

The collapsible portion is formed from any suitable flexible material known to the person skilled in the art. Preferably the flexible material is a foil material such as laminated foil material. Further preferably the laminated foil material comprises at least one metallic layer, such as an aluminium layer. Laminated metallic foil material allows for hermetic sealing of the cartridge and therefore offers excellent protection of the aerosol-generating liquid The flexible material preferably has a flexural modulus between 0.01 and 4 GPa, preferably between 0.02 and 2 GPa, for example between 0.05 and 1 GPa.

Youngs modulus and the flexural modulus are determined according to ASTM methods D790 and D6272, respectively.

In a further preferred embodiment, the collapsible portion of the cartridge is protected by a rigid housing. The rigid housing may be attachable to the rigid support portion and may partly or fully surround the collapsible portion. For example, the housing can be a rigid mesh of plastic or metallic material. When the housing fully surrounds the collapsible portion a hole or an air valve can be provided in order to allow for pressurization of the space between the collapsible portion and the housing during use of the cartridge. In a further embodiment means for actively adjusting the air pressure between housing and the collapsible portion can be provided in order to apply in a controlled manner slight overpressure to the collapsible portion and to thereby enhance liquid flow out of the cartridge.

The rigid support portion and the housing may sealingly surround the collapsible portion. The housing may be provided with a one-way valve for pressurization purposes. The collapsible portion may be made from an elastic balloon-like membrane. The advantage of such balloon-like membrane may be its tendency to contract back to its original shape pushes the liquid out of the cartridge without the need of an additional active means for creating pressure on the collapsible portion. By adjusting the one-way valve, contraction of the balloon-like membrane can be controlled.

The cartridge may comprise a heater element. Preferably, the heater element is attached to the rigid support portion. Preferably the heater element is a coil wire. Preferably the coil wire is provided near the nozzle of the rigid support portion. Preferably at least a portion of the wick extends from the nozzle and the coil wire is tightly wound around the portion of the wick extending from the nozzle. In this way intimate contact between the heating element and the wick carrying the aerosol-generating liquid is established providing for optimal vaporization conditions. Preferably the heater element is in electrically contacted to two electrodes provided at the rigid support portion. The electrodes may be provided at the front face of the rigid support portion at either side of the nozzle. Alternatively the electrodes can also be provided at the sides of the rigid support portion.

Preferably the collapsible portion is attached to the rigid support portion by thermo-sealing, welding, ultrasonic welding, glueing, or bonding. Choice of attachment methods also depends on the material chosen for the collapsible portion and the rigid support portion.

Preferably the support portion comprises a plurality of elevated stripes, whereby the sealing is provided between the elevated stripes and the collapsible portion. Each sealing stripe may be designed such that it theoretically provides full sealing between the collapsible portion and the rigid support portion. However, by providing a plurality of sealing stripes safety of the connection between the collapsible portion and the rigid support portion is increased.

The present invention also is directed to an aerosol generating system comprising the cartridge as disclosed herein. Preferably the aerosol-generating system is an electrical smoking system or an e-cigarette. The aerosol-generating system preferably comprises receiving means for mounting cooperation with the attachment means of the cartridge. The receiving means allow for easy mounting and removing of the cartridge within the housing of the aerosol generating system.

The aerosol generating system preferably further comprises a power source, and control circuitry. Preferably, the receiving means comprise electronic contacts for electrically contacting the electronic contacts provided at the rigid support portion of the cartridge such that the power source is in electric contact with heater element, when the cartridge is placed in the aerosol generating system.

The present invention is also directed to a method for manufacturing a cartridge suitable for use in aerosol generating systems. The method comprises the steps of providing a rigid support portion, with a nozzle defining an opening, attaching a collapsible portion to the rigid support portion to form a liquid storage portion, and providing a wick in the nozzle of the rigid support portion.

The invention will be further described, by way of example only, with reference to the accompanying drawings in which.

Figure 1:
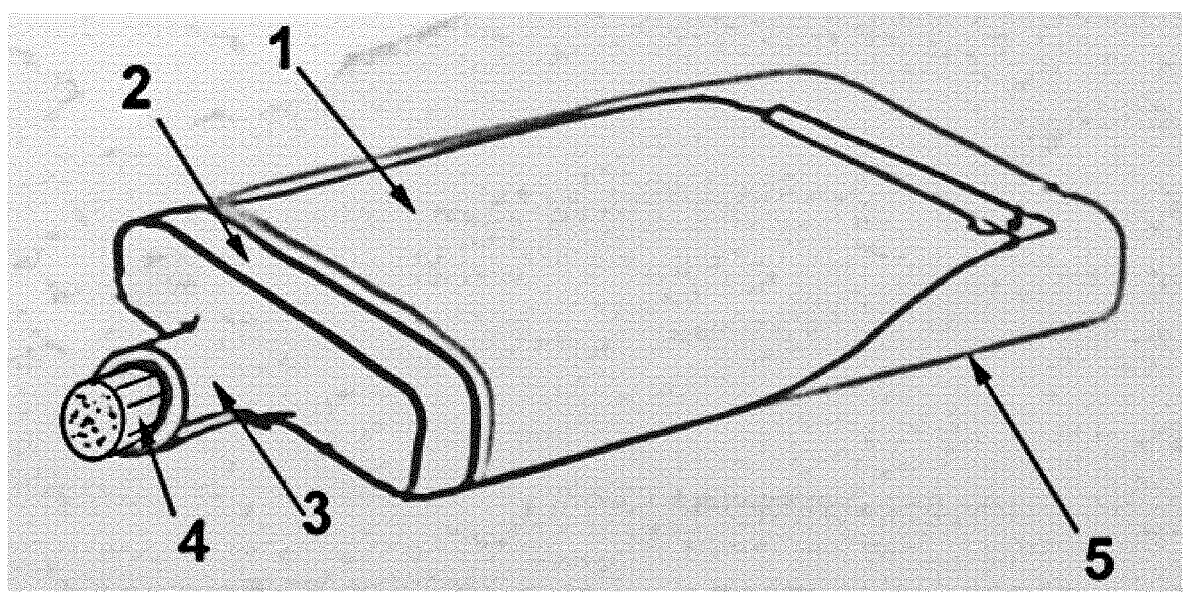
FIG. 1 shows a cartridge according to the present invention.

An embodiment of the cartridge of the present invention is depicted in FIG. 1. The cartridge comprises a collapsible portion 1 made of FEP foil laminated with aluminum and PVC which is sealingly connected to a rigid support portion 2. The rigid support portion 2 is made from Barex or FEP, and exhibits a nozzle 3 defining an opening through which liquid aerosol-generating substrate is released. A wick made from aramid fibers is provided within the opening of the nozzle. In order to protect the collapsible portion a housing 5 made from a polymeric compound with mechanical properties assuring rigidity at operating temperatures, such as PP, PEP, or PVC is provided, which surrounds the collapsible portion 1 and is fixed to the rigid support portion 2.

Figure 2:
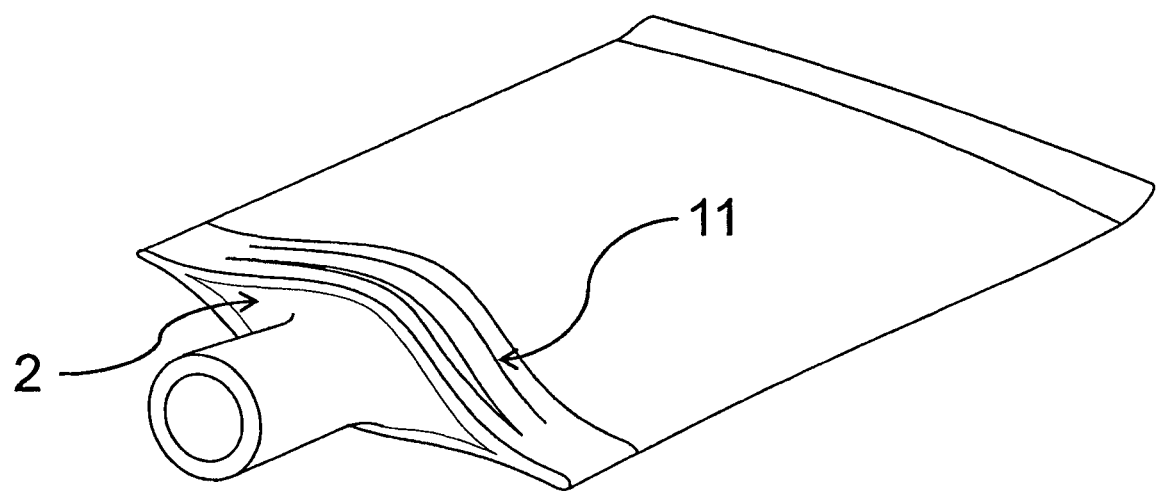
FIG. 2 shows details of the sealing area between the rigid support portion and the collapsible portion of the cartridge.

The connection between the rigid support portion 2 and the collapsible portion 1 is facilitated via thermo sealing. To this end the open end of the collapsible portion 1 is slipped over the circumference of the rigid support portion 2. As depicted in FIG. 2, a plurality of sealing stripes 11 are formed between the collapsible portion 1 and the rigid support portion 2. Each of the sealing stripes 11 provides proper sealing. By establishing a plurality of sealing stripes 11, secure sealing can be safeguarded even if one of the sealing stripes 11 should accidentally be damaged or exhibit manufacturing defects.

Figure 3:
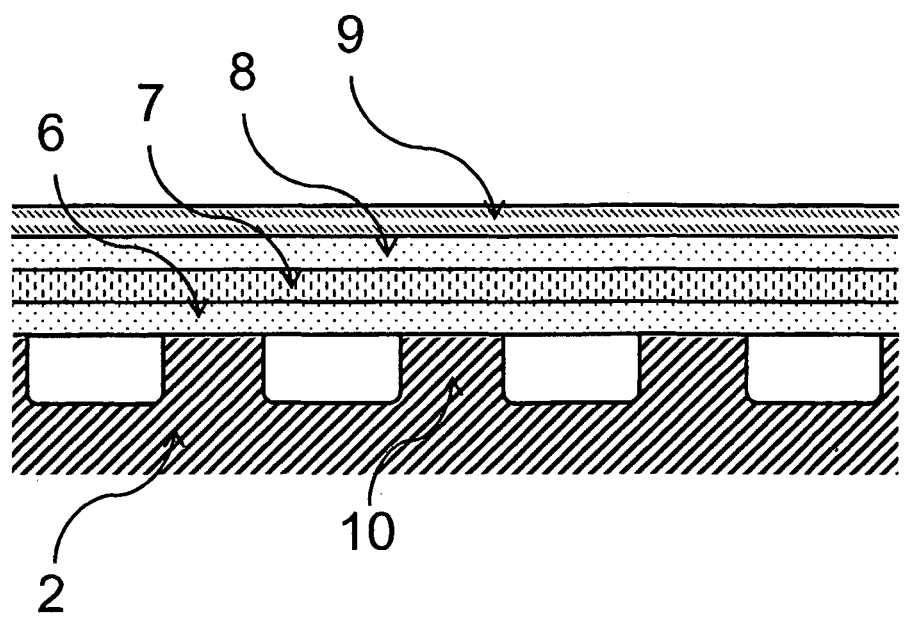
FIG. 3 shows a cross-sectional view of the sealing area of the cartridge.

FIG. 3 depicts a cross-section of the sealing area. The rigid support portion 2 comprises elevated areas 10 on which the thermo sealing to the collapsible portion 1 is established. The collapsible portion 1 is a layered structure comprising an aluminium layer 7, located between two polymeric layers 6, 8. The polymeric layers 6, 8 protect the aluminium layer 7 and allow for thermo sealing of the collapsible portion 1. The aluminium layer ensures hermetic sealing of the cartridge and thus preserves the aerosol-generating liquid from detrimental environmental influences. Outside layer 9 is an additional polymeric layer that is used for printing and branding purposes and in order to indicate the contents of the cartridge.

Figure 4:
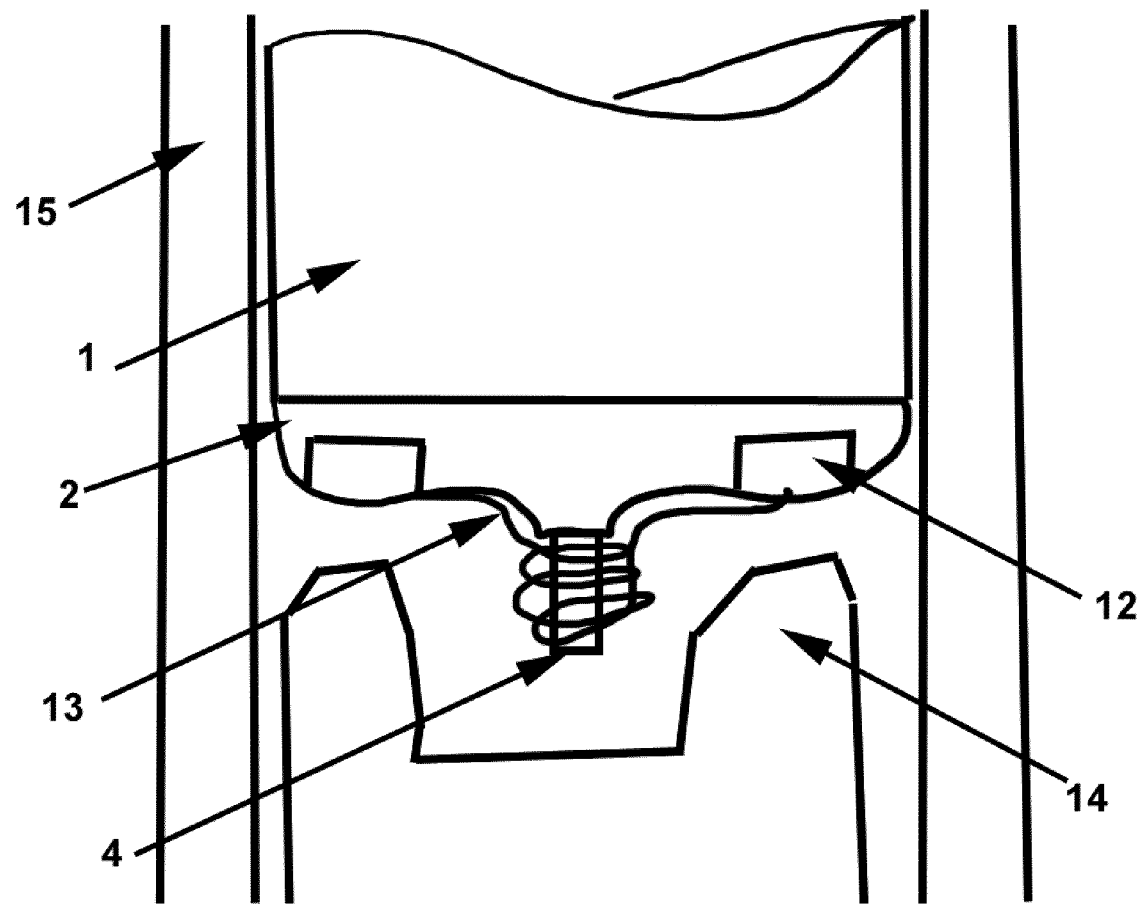
FIG. 4 shows a cartridge according to the present invention comprising a heater element.

The cartridges can be used in aerosol-generating systems such as e-cigarettes. In FIG. 4 a further embodiment of a cartridge mounted in a housing 15 of an e-cigarette is depicted. The cartridge again comprises a rigid support portion 2 and a collapsible portion 1. The rigid support portion comprises a nozzle defining an opening. A wick 4 is provided in the opening of the nozzle. The rigid support portion 2 further comprises electric contacts 12 provided at either side of the nozzle. The electric contacts 12 are connected to a heater element 13. The heater element 13 is a wire coil that is wound around the portion of the wick 4 extending out of the nozzle of the rigid support portion 2 of the cartridge. When the cartridge is mounted in the housing 15 of an e-cigarette, the electric contacts 12 of the rigid support portion 2, are connected to corresponding electric contacts 14 provided in the interior of the e-cigarette. Via electric contacts 14 the heating element is connected to a control circuitry (not shown) and a power source (not shown) provided in the interior of the e-cigarette. The wire coil is closely wound around the wick and therefore allows for excellent vaporization of the aerosol-generating liquid comprised in the wick.

Figure 5:
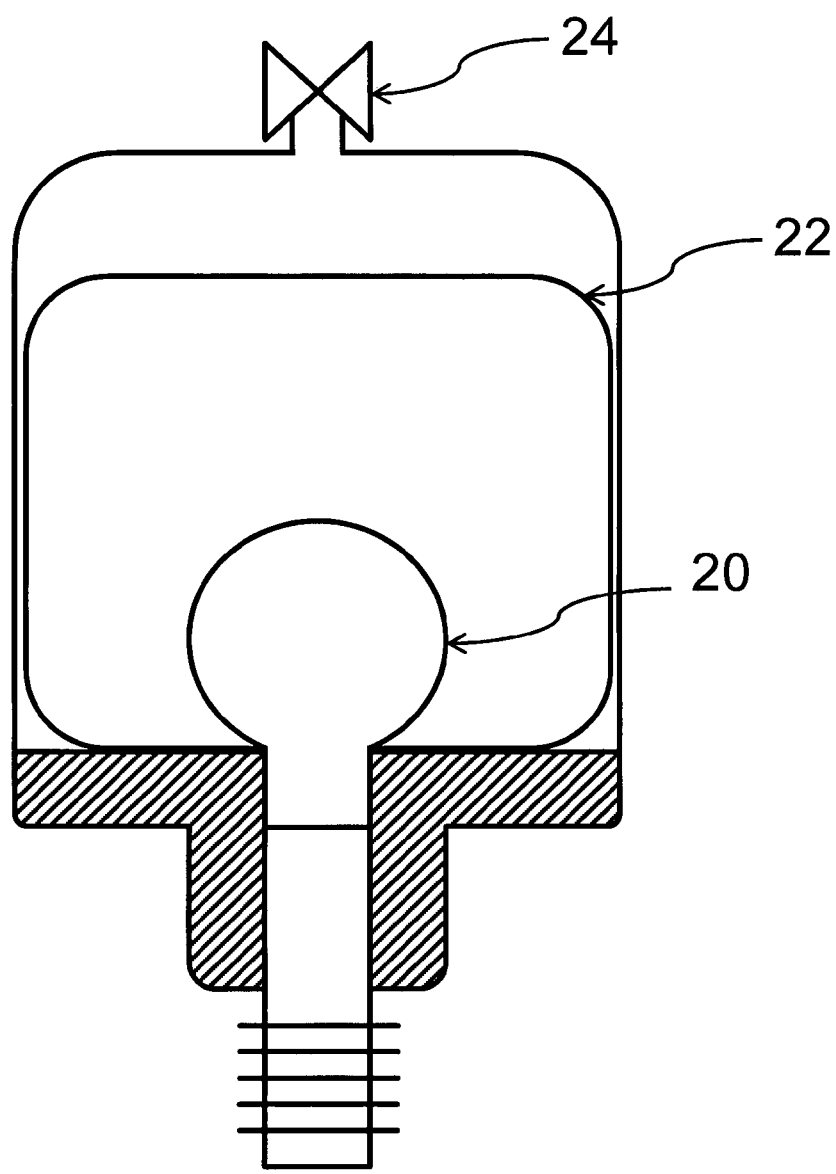

FIG. 5 shows an embodiment of the invention in which the collapsible portion is protected by a housing and in which the housing is sealingly connected to the rigid support portion. The collapsible portion is an elastic balloon-like member. Its initial form i.e. when the collapsible portion is empty is marked with reference numeral 20 in FIG. 5. Upon filling aersol-generating liquid into the cartridge the collapsible portion expands until it fills the internal volume of the cartridge. The expanded collapsible portion is depicted with reference numeral 22 in FIG. 5. In order to avoid that the expanded collapsible portion immediately returns into its initial form and to avoid uncontrolled spillage of the aerosol-generating liquid, the housing comprises a one-way valve 24. The one-way valve 24 is electronically controlled by an electric circuitry (not shown) and by activating the one-way valve 24 collapsing of the collapsible portion can be controlled. By preventing collapse of the collapsible portion, capillary action of the wick is hampered. By allowing collapse of the collapsible portion, capillary action of the wick is enhanced.

The invention claimed is:

1. A cartridge for an aerosol-generating system, the cartridge comprising:
   a liquid storage portion comprising
      a rigid support portion having a nozzle defining an opening configured to dispense an aerosol-forming substrate, and
      a collapsible portion attached to the rigid support portion;
   a wick disposed in the nozzle of the rigid support portion and within the opening, the wick extending across a full cross-section of the opening; and
   a heater element disposed at the rigid support portion,
   wherein the rigid support portion comprises two electrodes configured to contact the heating element and being disposed at opposite sides of the nozzle.

2. The cartridge according to claim 1, wherein the wick is a porous material and/or a fibrous material.

3. The cartridge according to claim 2, wherein the fibrous material is at least one material of aramid fibers, glass fibers, para-aramid synthetic fibers, and metallic fibers.

4. The cartridge according to claim 1, wherein the rigid support portion is a solid polymer material.

5. The cartridge according to claim 4, wherein the solid polymer material is at least one material of a duroplastic material, a thermosetting material, a heat-resistive material, and a ceramic material.

6. The cartridge according to claim 1, wherein the rigid support portion comprises an attachment portion configured to attach the cartridge in an aerosol-forming chamber of an aerosol-generating system.

7. The cartridge according to claim 1, further comprising a re-closable cap configured to close the opening of the nozzle and to prevent evaporation of an aerosol-generating liquid stored in the cartridge outside of an aerosol-generating system.

8. The cartridge according to claim 1, wherein the collapsible portion is a foil material.

9. The cartridge according to claim 8, wherein the foil material is a laminated foil material including at least one aluminum layer configured to hermetically seal the cartridge.

10. The cartridge according to claim 1, further comprising a rigid housing surrounding the collapsible portion and being configured to protect the collapsible portion.

11. The cartridge according to claim 1, wherein the heater element is a coil wire wound around a portion of the wick extending from the nozzle.

12. An aerosol-generating system, comprising:
   a cartridge comprising
      a liquid storage portion, the liquid storage portion comprising
         a rigid support portion having a nozzle defining an opening configured to dispense an aerosol-forming substrate, and
         a collapsible portion attached to the rigid support portion;
      a wick disposed in the nozzle of the rigid support portion and within the opening, the wick extending across a full cross-section of the opening; and
      a heater element disposed at the rigid support portion,
      wherein the rigid support portion comprises two electrodes configured to contact the heating element and being disposed at opposite sides of the nozzle.

13. The aerosol-generating system according to claim 12, further comprising receiving means for mounting cooperation with an attachment portion configured to attach the cartridge in an aerosol-forming chamber of the aerosol-generating system.

14. The aerosol-generating system according to claim 13, further comprising a power source and control circuitry, the receiving means comprising electronic contacts configured to contact the two electrodes disposed at the rigid support portion of the cartridge such that the power source is configured to be in electrical contact with the heater element when the cartridge is disposed in the aerosol-generating system.

15. A method for forming a cartridge, comprising:
   providing a rigid support portion with a nozzle defining an opening;
   attaching a collapsible portion to the rigid support portion to form a liquid storage portion;
   providing a wick in the nozzle of the rigid support portion and within the opening, the wick extending across a full cross-section of the opening; and
   providing a heater element at the rigid support portion,
   wherein the rigid support portion comprises two electrodes configured to contact the heating element and being disposed at opposite sides of the nozzle.

\* \* \* \* \*